(12) United States Patent
He et al.

(10) Patent No.: US 7,012,063 B2
(45) Date of Patent: Mar. 14, 2006

(54) REDUCING AXON DEGENERATION WITH PROTEASOME INHIBITORS

(75) Inventors: Zhigang He, Boston, MA (US); Qiwei Zhai, Boston, MA (US); Jing Wang, Boston, MA (US); Ryan Watts, Stanford, CA (US); Eric Hoopfer, Stanford, CA (US); Liqun Luo, Stanford, CA (US)

(73) Assignee: Children's Medical Center Corporation, Boston, MA (US)

( * ) Notice: Subject to any disclaimer, the term of this patent is extended or adjusted under 35 U.S.C. 154(b) by 384 days.

(21) Appl. No.: 10/461,778

(22) Filed: Jun. 13, 2003

(65) Prior Publication Data

US 2004/0254118 A1 Dec. 16, 2004

(51) Int. Cl.
*A01N 37/18* (2006.01)
*A01N 43/04* (2006.01)
*A61K 38/00* (2006.01)
*C07K 14/00* (2006.01)

(52) U.S. Cl. .............................. 514/2; 514/2; 514/125; 530/300

(58) Field of Classification Search .................... None
See application file for complete search history.

(56) References Cited

*Primary Examiner*—Bruce R. Campell
*Assistant Examiner*—Satyanarayana R. Gudibande
(74) *Attorney, Agent, or Firm*—Richard Aron Osman

(57) ABSTRACT

Reduced degeneration of an axon predetermined to be subject to degenerative neuropathy in a term patient is effected by contacting the axon in situ with an effective amount of a ubiquitin-proteasome system (UPS) inhibitor sufficient to reduce degeneration of the axon; and detecting a resultant reduction in the degeneration of the axon in situ.

19 Claims, No Drawings

REDUCING AXON DEGENERATION WITH PROTEASOME INHIBITORS

This work was supported by Federal Grant No. 1R21NS41999-01 from NINDS, No. 1R01NS42252 from NIDA and No. R01-NS41044 from NIH. The government may have rights in any patent issuing on this application.

FIELD OF THE INVENTION

The invention is in the field of reducing axon degeneration with proteasome inhibitors.

BACKGROUND OF THE INVENTION

Axon degeneration occurs frequently in many types of chronic neurodegenerative diseases and in injuries to axons caused by toxic, ischemic, or traumatic insults (Raff et al., 2002; Coleman and Perry, 2002). It may lead to separation of the neuron from its targets, resulting in loss of neuronal function. In the past, much effort has been focused on understanding the nature of neuronal cell death in these diseases (reviewed by Yankner and Yuan, 2001). However, strategies designed to prevent neuronal cell death have resulted in only limited success in preventing or delaying neurodegeneration (reviewed by Friedlander, 2003). One possibility is that neuronal cell death occurs too late in these diseases so that it may not be an efficient target for therapy. Thus, interfering with the process of axon degeneration may represent an additional and complementary therapeutic avenue for these diseases.

One model of axon degeneration is the self-destructive process observed at the distal portion of a transected axon upon injury, termed Wallerian degeneration (Waller, 1850). In vertebrates, the distal part of an axon can remain viable and conduct action potentials in vivo for up to a few days, after which it undergoes a rapid structural destruction where the axolemma and axonal cytoskeleton are dismantled (reviewed by Griffin et al., 1995; Gillingwater and Ribchester, 2001). Morphologically, such a degenerative process is characterized by a beading appearance followed by granular disintegration of the axons (reviewed by Griffin et al., 1995; Gillingwater and Ribchester, 2001). Axons undergoing Wallerian degeneration do not evidence detectable activation of the caspase family cysteine proteases (Finn et al., 2000), though calpain proteases appear to be activated (Glass et al., 2002).

Because most neuronal proteins are synthesized in the soma and carried to the axon by specialized axonal transport systems, degeneration of the transected axons has long been thought to result from starvation of necessary proteins and other materials. However, the recent discovery of a spontaneously occurring mutant mouse strain, C57BL/Wld$^s$, whose axons survived for as long as weeks after transection (Lunn et al., 1989; Perry et al., 1990a; Glass et al., 1993), suggests that Wallerian degeneration involves an active and regulated auto-destruction program.

The Wld$^s$ phenotype has been attributed to the overexpression of a fusion protein (Mack et al., 2001) that consists of an intact nicotinamide mononucleotide adenylyltransferase (Nmnat) (Conforti et al., 2000), which functions in the synthetic pathway for adenine dinucleotide (NAD+), fused to 70 N-terminal amino acids of UFD2, an E4 protein involved in poly-ubiquitination (Koegl et al., 1999). The fusion gene is highly expressed in the Wld$^s$ nervous system, and induces a Wld$^s$ phenotype when expressed in wild-type mice. It is not known how it interferes with Wallerian degeneration (Mack et al., 2002): the N-terminal portion is but a tiny fragment of the native 1173 amino acid UFD2, and this fragment is absent in the functionally conserved homologue of UFD2 in yeast (Koegl et al., 1999), so functional significance of this fragment is not apparent. And although the fusion protein retains Nmnat activity, there are conflicting unpublished data on deletion mutant function (Coleman et al., 2002; Raff et al., 2002; He et al., 2003). In any event, the fusion protein is primarily nuclear, so it presumably acts indirectly to protect axons. (Mack et al., 2001).

The ubiquitin proteasome system (UPS) has been implicated as a common mechanism for selective protein degradation in a variety of biological processes, such as axonal pathfinding (Campbell and Holt, 2001, 2003) and synapse formation (for example, DiAntonio et al., 2001). UPS disruption has been associated with numerous pathologies, particularly neuropathies. For example, an intragenic deletion in the gene encoding ubiquitin carboxy-terminal hydrolase causes the axon degeneration phenotype of the gracile axonal dystrophy (gad) mouse (Saigoh et al., 1999). Furthermore, the UPS is involved in neurodegenerative diseases such as Alzheimer's, Parkinson's and poly-glutamine repeat diseases, wherein a common feature is the abnormal accumulation of proteins in plaques (Miller and Wilson, 2003). Inhibiting the UPS may enhance the pathogenic accumulation of proteins (Bence et al, 2001), and several neurodegenerative diseases appear to be caused by genetic mutations that inhibit the UPS (Miller and Wilson, 2003).

Nevertheless, proteasome inhibition has been a proposed therapeutic strategy for treating cancer, reperfusion injury, and inflammatory diseases like asthma, rheumatoid arthritis, multiple sclerosis and psoriasis (Elliot et al., 2003, J Mol Med 81, 235–45; Pye et al., 2003, Am J Physiol Heart Circ Physiol 284, H919–26; Elliot et al., 2001, Am J Clin Pathol 116, 637–46; Phillips et al., 2000, Stroke 31, 1686–93). Here we report that pharmacological inhibition of the UPS can delay axon degeneration associated with a variety of neuropathies, particularly acute neuropathies, apparently by stabilizing microtubules.

SUMMARY OF THE INVENTION

The invention provides methods and compositions for reducing degeneration of an axon predetermined to be subject to degenerative neuropathy in a term patient. In general, the methods comprise: contacting the axon in situ with an effective amount of a ubiquitin-proteasome system (UPS) inhibitor sufficient to reduce degeneration of the axon; and detecting a resultant reduction in the degeneration of the axon in situ. In preferred embodiments, the contacting step is necessary and sufficient to effect the resultant reduction in degeneration, so the method consists or consists essentially of the recited contacting and detecting steps.

In particular embodiments, the inhibitor is a proteasome inhibitor, preferably a reversible peptide aldehyde such as MG132 or an irreversible modifier like lactacystin and clasto-lactacystin β-lactone. In yet additional embodiments, the inhibitor is delivered in conjunction with a synergizing microtubule stabilizer like taxol.

The degenerative neuropathy is preferably axon trauma, such as axotomy, though it may also result from other neurodegenerative disease, and may occur in the absence of substantial necrosis or cell death.

The contacting step is preferably effected by local, regionally restricted delivery at the axon, preferably not contacting the neuron cell body. The contacting step may also be preceded by a diagnostic step.

DESCRIPTION OF PARTICULAR EMBODIMENTS OF THE INVENTION

The following descriptions of particular embodiments and examples are offered by way of illustration and not by way of limitation. Unless contraindicated or noted otherwise, in these descriptions and throughout this specification, the terms "a" and "an" mean one or more, the term "or" means and/or and polynucleotide sequences are understood to encompass opposite strands as well as alternative backbones described herein.

The invention provides methods of reducing degeneration of an axon predetermined to be subject to degenerative neuropathy in a term patient. In general, the methods comprise: contacting the axon in situ with an effective amount of a ubiquitin-proteasome system (UPS) inhibitor sufficient to reduce degeneration of the axon; and detecting a resultant reduction in the degeneration of the axon in situ.

The inhibitor effectively inhibits the UPS present in the target axon. A wide variety of suitable inhibitors may be employed, guided by art-recognized criteria such as efficacy, toxicity, stability, specificity, half-life, etc. The inhibitor is functionally defined, and may interfere at any point in the axon's UPS; as examples, suitable inhibitors include inhibitors of ubiquitin activating enzyme (E1), ubiquitin conjugating enzyme (E2) or ubiquitin ligase (E3) inhibitor. In preferred embodiments, the inhibitor is a proteasome inhibitor, which may target any domain of the axon's proteasome, including the 19S regulatory domain and the 20S core.

Any of a wide variety of established strategies for inhibiting intracellular catalytic pathways may be used, including RNA-based reagents, such as RNAi and antisense reagents, protein and peptide-based reagents, such as dominant-negative deletion mutants, antibodies and fragments thereof, including Fab fragments and intrabodies, competitive peptides, including E2 or E3 peptide blockers, and small molecule reagents, like reversible peptide aldehydes such as MG132 or irreversible modifiers like lactacystin and clasto-lactacystin β-lactone.

Preferred proteasome inhibitors include Velcade (PS-341) and PS-519 (Elliot, et al., Am J Clin Pathol. 2001 November; 116(5):637–46; Soucy, et al. J. Am. Chem. Soc.,121 (43), 9967–9976, 1999), and proteasome inhibitory (+)-lactacystin-β-lactone analogs; for structure-activity relationships (SAR) data summary, see Table 1 of Masse et al., Eur J Org Chem 2000, 2513–28. Alternative pharmacologically acceptable inhibitors effective in the disclosed methods are readily screened from the wide variety of UPS inhibitors known in the art using the disclosed in vivo protocols. For example, a panel of proteasome inhibitors comprising inhibitors effective in the disclosed protocols and commercially available is provided below.

Proteasome inhibitors referenced by Calbiochem (San Diego, Calif.) catalog numbers:

| | | | |
|---|---|---|---|
| 539162 | (Benzyloxycarbonyl)-Leu-Leu-phenylalaninal | 474790 | Z-LLL-CHO |
| 371715 | 2,3,5a,6-Tetrahydro-6-hydroxy-3(hyroxymethyl)-2-methyl-10H-3a,10a-epidithio-pyrazinol[1,2 α]indole-1,4-dione | 438185 | Lovastatin |
| 492025 | 4-Hydroxy-3-nitrophenylacetyl-Leu-Leu-Leu-vinyl sulfone | 426104 | α-Methyl-clasto-Lactacystin β-Lactone |
| 482240 | 4-Hydroxy-5-iodo-3-nitrophenylacetyl-Leu-Leu-Leu-vinylsulfone | 426104 | α-Methylomuralide |
| 688500 | Ac-hFLFL-epoxide | 438185 | Mevinolin |
| 112270 | Aclacinomycin A, Streptomyces galilaeus | 208719 | MG 101 |
| 112270 | Aclarubicin | 474780 | MG-115 |
| 112270 | ACM | 474790 | MG-132 |
| 114802 | AdaAhx3L3VS | 474791 | MG-132 in Solution |
| 114803 | AdaK(Bio)AhX3L3VS | 539163 | MG-262 |
| 114803 | AdaLys(Bio)Ahx3L3 VS | 438185 | MK-803 |
| 114802 | Adamantane-acetyl-(6-aminohexanoyl) 3-(leucunyl)3-vinyl-(methyl)-sulfone | 482240 | NIP-L3VS |
| 208721 | ALLM | 482240 | NLVS |
| 208719 | ALLN | 492025 | NP-L3VS |
| 208719 | Calpain Inhibitor I | 492025 | NP-LLL-VS |
| 208721 | Calpain Inhibitor II | 426102 | Omuralide |
| 474790 | Carbobenzoxy-L-leucyl-L-leucyl-L-leucinal | 529643 | PR-11 |
| 474780 | Carbobenzoxy-L-leucyl-L-leucyl-L-norvalinal | 529645 | PR-39, Porcine, Synthetic |
| 324800 | Epoxomicin, Synthetic | 539160 | Proteasome Inhibitor I |
| 371715 | Gliotoxin, Gladiocladium fimbriatum | 539162 | Proteasome Inhibitor II |
| 657008 | Isovaleryl-L-tyrosyl-L-valyl-DL-tyrosinal | 539163 | Proteasome Inhibitor III |
| 426100 | Lactacystin, Synthetic | 539175 | Proteasome Inhibitor IV |
| 426102 | clasto-Lactacystin β-Lactone | 539164 | Proteasome Inhibitor Set I |
| 474780 | Z-LL-Nva-CHO | 539165 | Proteasome Inhibitor Set II |
| 662056 | Ubiquitin Aldehyde | 539160 | PSI |
| 688500 | YU101 | 557550 | Ro106-9920 |
| 539175 | Z-GPFL-CHO | 557551 | Ro106-9920, Control |
| 539162 | Z-LLF-CHO | 529643 | RRRPRPPYLPR |
| 539163 | Z-LLL-B(OH)2 | 657008 | Tyropeptin A, Synthetic |

Detailed protocols for implementing the recited steps are exemplified below and/or otherwise known in the art as guided by the present disclosure. The recited contacting/delivering and detecting steps are tailored to the selected system. More detailed such protocols are described below. Similarly, the detecting step is effected by evaluating any suitable metric of axon degeneration, such as evaluated by visual inspection, optical imaging, host mobility or other indicative host function, etc. Reduced degeneration is relative to that of an otherwise identical untreated axon subject to similar degeneration. Hence, reduced degeneration may be detected as slowed degeneration, no degenerative progress, or regenerative progress.

The target cells are injured mammalian, preferably human, preferably not embryonic, preferably term, preferably adult neurons in situ, e.g. Schulz M K, et al., Exp Neurol. 1998 February; 149(2): 390–397; Guest J D, et al., J Neurosci Res. 1997 Dec. 1; 50(5): 888–905; Schwab M E, et al., Spinal Cord. 1997 Jul.; 35(7): 469–473; Tatagiba M, et al., Neurosurg 1997 March; 40(3): 541–546; and Examples, below. The methods may be applied to any degenerative neuropathy, particularly acute disorders, such as stroke, trauma, etc. As demonstrated with numerous validated animal models, other neurodegenerative diseases, even chronic neuropathies involving plague formation, such as multiple sclerosis are also targetable with the disclosed methods. In many cases, these models indicate that therapeutic administrations are preferably acute or punctuated, and/or target relatively specific UPS components, such as E2/E3. Acute therapies are typically delivered over fewer than 18 weeks, preferably fewer than 6 weeks, more preferably few than 2 weeks. Additional particular applications are where the neuropathy does not evidence substantial neuro-necrosis or neuron cell-death. The target cell may be presently subject to the neuropathy or degeneration, or subject to a defined predisposition toward the neuropathy or degeneration.

Compositions comprising the recited inhibitor may be administered by any effective route compatible with therapeutic activity of the compositions and patient tolerance. For CNS administration, a variety of techniques is available for promoting transfer of therapeutic agents across the blood brain barrier including disruption by surgery or injection, drugs which transiently open adhesion contact between CNS vasculature endothelial cells, and compounds which facilitate translocation through such cells. The compositions may also be amenable to direct injection or infusion, intraocular administration, or within/on implants e.g. fibers such as collagen fibers, in osmotic pumps, grafts comprising appropriately transformed cells, etc.

In a particular embodiment, the inhibitor is delivered locally and its distribution is restricted. In particular embodiments, the neuron cell body is not contacted. For example, a particular method of administration involves coating, embedding or derivatizing fibers, such as collagen fibers, protein polymers, etc. with therapeutic agents, see also Otto et al. (1989) J Neurosci Res. 22, 83–91 and Otto and Unsicker (1990) J Neurosc 10, 1912–1921. The amount of inhibitor administered depends on the agent, formulation, route of administration, etc. and is generally empirically determined, and variations will necessarily occur depending on the target, the host, and the route of administration, etc.

In yet additional embodiments, the inhibitor is delivered in conjunction with a synergizing nuclear stabilizer, particularly a microtubule stabilizer like taxol. The compositions may be advantageously used in conjunction with other neurogenic agents; neurotrophic factors, growth factors, anti-inflammatories, antibiotics etc.; and mixtures thereof, see e.g. *Goodman & Gilman's The Pharmacological Basis of Therapeutics*, 9th Ed., 1996, McGraw-Hill. Exemplary such other therapeutic agents include neuroactive agents such as in Table 1.

TABLE 1

Neuroactive agents which may be used in conjunction with UPS inhibitors.

| NGF | Heregulin | Laminin |
|---|---|---|
| NT3 | IL-3 | Vitronectin |
| BDNF | IL-6 | Thrombospondin |
| NT4/5 | IL-7 | Merosin |
| CNTF | Neuregulin | Tenascin |
| GDNF | EGF | Fibronectin |
| HGF | TGFa | F-spondin |
| bFGF | TGFb1 | Netrin-1 |
| LIF | TGFb2 | Netrin-2 |
| IGF-I | PDGF BB | Semaphorin-III |
| IGH-II | PDGF AA | L1-Fc |
| Neurturin | BMP2 | NCAM-Fc |
| Perceptin | BMP7/OP1 | KAL-1 |

Abbreviations:
NGF, nerve growth factor;
NT, neurotrophin;
BDNF, brain-derived neurotrophic factor;
CNTF, ciliary neurotrophic factor;
GDNF, glial-derived neurotrophic factor;
HGF, hepatocyte growth factor;
FGF, fibroblast growth factor;
LIF, leukemia inhibitory factor;
IGF, insulin-like growth factor;
IGH, insulin-like growth homone;
IL, interleukin;
EGF, epidermal growth factor;
TGF, transforming growth factor;
PDGF, platelet-derived growth factor;
BMP, bone morphogenic protein;
NCAM, neural cell adhesion molecule;
KAL-1, Kallman syndrome gene-1.

In particular embodiments, the inhibitor is administered in combination with a pharmaceutically acceptable excipient such as sterile saline or other medium, gelatin, an oil, etc. to form pharmaceutically acceptable compositions. The compositions and/or compounds may be administered alone or in combination with any convenient carrier, diluent, etc. and such administration may be provided in single or multiple dosages. Useful carriers include solid, semi-solid or liquid media including water and non-toxic organic solvents. As such the compositions, in pharmaceutically acceptable dosage units or in bulk, may be incorporated into a wide variety of containers, which may be appropriately labeled with a disclosed use application. Dosage units may be included in a variety of containers including capsules, pills, etc. Dosage amounts are dictated by the targeted neuropathy, the selected inhibitor and selected route of administration, determined empirically and guided by prior usages of the selected inhibitor or similar reagents, including the examples provided below. For example, non-peptidyl inhibitors (e.g. lactacystin, α-methylomuralide, PS-519 and PS-341) are typically active at relatively low dosages when systemically administered. PS-341, for example, may be administered as a bolus intravenous injection 1.3 mg/m$^2$/dose twice weekly for two weeks. For local, regionally-restricted delivery, dosages will also depend on the mode of delivery (embedded fibers, osmotic pump, etc.), but will typically be in the range of 1 ng-1 mg/kg/day.

The invention also provides pharmaceutical screens for modulators, particularly enhancers or synergizers of disclosed UPS inhibitor-mediated axon degeneration reduction, particularly, methods for characterizing an agent as modulating such degeneration reduction by practicing the disclosed methods in the presence of a candidate agent, whereby but for the presence of the agent, the axon provides a reference degeneration; measuring an agent-biased degeneration of the axon; and comparing the reference and agent-biased degeneration, wherein a difference between the reference and agent-biased degeneration indicates that the agent modulates UPS inhibitor-mediated degeneration reduction.

The invention also provides compositions and mixtures specifically tailored for practicing the subject methods, including implantable, injectable or otherwise deliverable gelfoams, fibers, pumps, stents, or other devices loaded with premeasured, discrete and contained amounts of UPS inhibitor and specifically suited, adapted and/or tailored for the recited CNS axon delivery. Kits for practicing the disclosed methods may also comprise printed or electronic instructions describing the applicable subject method.

EXAMPLES

Inhibiting the Ubiquitin-Proteasome Pathway Delays Wallerian Degeneration.

Wallerian degeneration in most transected mammalian nerve fibers is a complex sequence that entails degradation of the axon, changes in the ensheathing and glial cells, alterations in the blood-tissue barriers, and responses of macrophage-lineage cells (reviewed by Griffin et al., 1995). To study the underlying mechanisms involved in the axon degeneration process, we have used the degeneration of transected axons from cultured primary neurons as models (Buckmaster et al., 1995; George et al., 1995; Wang et al., 2001). In cultured sympathetic ganglia derived from postnatal day 3 (p3) rats, soma-deprived axons undergo a typical degenerative process (herein, George et al., 1995; Wang et al., 2001). The severed axons first appear normal for 6–10 hr, depending upon the duration of culturing prior to axotomy. For sympathetic ganglia that have been cultured for 5 days, the severed axons begin to develop such signs of early degeneration as focal swelling and beading approximately 8 hrs after the axons had been separated from their cell bodies. In most cases, the axons would be completely degenerated and detached after 12–16 hr post-axotomy. Similar degenerative processes were also observed in other types of cultured neurons, such as chicken dorsal root ganglion neurons and retinal ganglion cells. Few associated non-neuronal cell nuclei were seen with transected axons undergoing Wallerian degeneration, indicating that the observed axon degeneration is independent of glial cells, consistent with the notion that an axon-intrinsic program operates during Wallerian degeneration (Perry et al., 1990b; Glass et al., 1993).

We examined whether UPS is involved in axotomy-triggered Wallerian degeneration by using specific pharmacological inhibitors. It is known that for UPS to degrade a specific substrate protein, the sequential action of three enzymes, including a ubiquitin activating enzyme (E1), a ubiquitin conjugating enzyme (E2), and a ubiquitin ligase (E3), is required to covalently link ubiquitin to the substrate. Poly-ubiquitinated proteins are then targeted for degradation by the 26S proteasome, which is composed of two 19S proteasome regulatory particles and a 20S core. Substrate ubiquitination may also be reversed by ubiquitin proteases (reviewed by Weissman, 2001). In spite of the existence of multiple E2 and E3 molecules, the final and common step in degrading polyubiquitinated protein substrates is through the 26S proteasome machinery. Consistent with previous evidence for the existence and functioning of the UPS in axons (Campbell and Holt, 2001, 2003), components of UPS machinery, such as subunit C2 of the proteasome 20S, were found in both intact and transected axons from sympathetic neurons. Thus, to perturb UPS activity we used two mechanistically different proteasome inhibitors, MG132, a peptide-based reversible proteasome inhibitor (Rock et al., 1994), and lactacystin, a synthetic irreversible proteasome inhibitor (Fenteany et al., 1995), both of which had been extensively used to inhibit UPS activity in many different cell types including cultured neurons (Campbell and Holt, 2001, 2003).

Dose-response studies (1–100 mM) were carried out for both MG132 and lactacystin and the most robust effects of both inhibitors were seen at concentration of 10–20 mM, a range frequently used in past studies (for example, Rock et al., 1994; Campbell and Holt, 2001). When included in sympathetic cultures, these proteasome inhibitors did not significantly alter the gross morphology of the uncut axon, but profoundly delayed the Wallerian degeneration process. Compared to untreated transected axons that began developing early signs of degeneration 8 hr post-axotomy, those treated with both MG132 and lactacystin did not show degeneration until 16 hr post-axotomy. 24 hr post-axotomy when most of the axon debris has detached from the culture surface in control cultures, proteasome inhibitor-treated explants still retained many axons with some degeneration signs, which remained up to 36 hr post-axotomy. This effect was specific for proteasome inhibitors, as the inclusion of a caspase inhibitor Z-VAD-fmk (Pronk et al., 1996) or a serine protease inhibitor pepstatin A (Sanchez et al., 1992) did not result in any detectable protective effect. Interestingly, such a protective effect only occurred when these proteasome inhibitors were added to the cultures prior to axotomy. As it is known that these inhibitors are able to quickly execute their inhibitory effects upon addition to the cultures (Ruckdeschel et al., 1998; Campbell and Holt, 2001), these results indicate a role of UPS in the early stages of Wallerian degeneration.

To provide additional evidence for the involvement of the UPS in Wallerian degeneration, we constructed recombinant herpes simplex viruses (HSV) to express in cultured sympathetic neurons a yeast ubiquitin protease (UBP2), which has been shown to reverse substrate ubiquitination across different species (Baker et al., 1992; DiAntonio et al., 2001; Watts et al., 2003). We found that sympathetic neurons infected with HSV expressing UBP2, but not control HSV, showed a significantly slower rate of degeneration. 8 hr post-axotomy, approximately 90% of axons from control HSV-infected explants, and only about 40% of axons from HSV-UBP2-infected ones, developed a beading appearance. However, the protective effects of UBP2 overexpression were less robust than those of the proteasome inhibitors, presumably due to the low expression levels of UBP2.

As previous studies have implicated calpains, a class of calcium-dependent proteases, in Wallerian degeneration (George et al., 1995; Finn et al., 2000), we also examined the contribution of calpain activity in our assays with specific calpain inhibitors such as ALLN (Finn et al., 2000). Consistent with previous studies (Finn et al., 2000), addition of ALLN (50 mM) did not affect the development of the axonal beading appearance, but slightly delayed the disintegration of transected axons into debris. 16 hr after axotomy when most of the transected axons from control cultures degenerated into debris, there were still remaining axon fibers in ALLN-treated cultures. The weak protective effects of ALLN and other calpain inhibitors were not likely to be due to residual calpain activity as the same treatments completely prevented the calpain-dependent degradation of neurofilaments NF160 and NF68 as detected by Western blotting. These results together indicate that UPS and calpains act on different stages of Wallerian degeneration. Application of the calcium chelator EGTA (2 mM) resulted in a much stronger protective effect on Wallerian degeneration than ALLN and other calpain inhibitors, though axon degeneration elicited by calcium ionophore A23187 or ionomycin were blocked by EGTA but not MG132.

Microtubule destabilization at the initiation stage of Wallerian degeneration in vitro. We next examined which cellular events might correlate with the involvement of UPS and calpains in Wallerian degeneration. We monitored the integrity of different subcellular organelles in the transected axons by both immunocytochemistry and membrane labeling. Plasma membrane staining with both a lipophilic dye DiI and antibodies against an axonal surface molecule p75, as well as cytoplasmic staining with an antibody against PGP9.5, an abundant axonal cytoplasmic protein (George et al., 1995; Finn et al., 2000, herein), revealed characteristic morphological changes of Wallerian degeneration, with the onset of swelling and beading followed by fragmentation and detachment of axonal debris. Likewise, immunostaining with an anti-neurofilament NF160 (2H3) antibody showed a similar time course of degeneration, consistent with previous observations that neurofilaments are broken down during Wallerian degeneration (Schlaepfer and Micko, 1978; Schlaepfer and Hasler, 1979; Kamakura et al., 1982; Schlaepfer et al., 1984; Finn et al., 2000). At the protein level, we observed a corresponding cleavage of the neurofilament subunits, neurofilament 160 (NF-160) and neurofilament 68 (NF68) as detected by Western blotting.

Apart from these axonal markers, however, the earliest detectable change appears to occur in the microtubules of transected axons. Immunostaining with antibodies against both a-tubulin and b-tubulin revealed fragmented microtubule structures in approximately 60% of the transected axons 4 hr after axotomy, when other subcellular structures were still largely intact as suggested by both phase contrast image analysis and immunostaining. After 12 hr post-axotomy, the stained signals of fragmented microtubule structures weakened gradually and were replaced by many spheroid bodies in severed axons. By 16 hr after axotomy, almost all of the detected signals were spheroid bodies along the tracts of original axons. Even 16 hrs after axotomy when the majority of the axonal NF160 and NF68 has been degraded, most of the tubulin proteins still remained intact and the protein level remained stable according to Western blotting. To provide additional biochemical evidence for such an axotomy-elicited microtubule destabilization in transected axons at early stages of Wallerian degeneration, we separated monomeric (soluble, S) and polymerized (pellet, P) tubulins from transected axons and measured the depolymerization ratio (S/[S+P]) at different time points. Microtubule depolymerization in transected axons was significantly increased as early as 4–8 hr post-axotomy. These results together indicate that the breakdown of neurofilaments and microtubules is mediated by different mechanisms, with neurofilament proteins being cleaved and microtubule polymers simply being disassembled.

UPS and calpains mediate the breakdown of axonal cytoskeleton components. To explore the link between these cellular and molecular changes during Wallerian degeneration, we next examined whether proteasome inhibitors, calpain inhibitors, and EGTA affect neurofilaments and microtubules in transected axons. Both proteasome inhibitors (MG132 and lactacystin) and the calcium chelator EGTA profoundly retarded the degeneration of all examined subcellular markers, including both the destabilization of microtubules and the cleavage of neurofilaments. On the other hand, ALLN only delayed neurofilament degradation, but not the fragmentation of microtubules. While confirming a critical involvement of calpains in the cleavage of neurofilaments (Schlaepfer and Micko, 1978; Schlaepfer and Hasler, 1979; Kamakura et al., 1982; Schlaepfer et al., 1984; Finn et al., 2000), these results also indicate that both calcium-dependent events and the UPS pathway are critical for the disassembly of microtubules.

Although proteasome inhibitors can also retard the degeneration of other axonal structures such as axolemma and neurofilaments, it is possible that these alterations are secondary to the disruption of microtubules in the transected axons. Consistently, we found that proteasome inhibitors cannot protect the Wallerian-like neurite degeneration elicited by microtubule destabilizing agents, such as colchicine (Andreu and Timasheff, 1986; Wilson and Farrell, 1986; Xie and Barrett, 1991) and vincristine (Luduena et al., 1986; Wang et al., 2001).

MG132 slows down Wallerian degeneration of transected optic nerve in vivo. To assess whether these observations from in vitro culture experiments hold true in vivo, we first performed immunostaining experiments to examine the alterations of microtubules and neurofilaments in transected optic nerves. In uncut optic nerves, antibodies against both neurofilament and tubulin components revealed numerous fiber structures of the axon cytoskeleton. In optic nerves 3 days after axotomy when an antibody against NF160 still detected many linear neurofilament fibers, the antibody against a neuron specific b-tubulin detected largely spheroid bodies, reminiscent of the microtubule changes observed in vitro 16 hr post-axotomy. Similar staining patterns were observed in transected optic nerves 7 or 14 days post-axotomy. As previous studies implicated neurofilament degradation as an early marker of Wallerian degeneration (for example, Glass et al., 2002), our results suggest that destabilization of microtubules might occur prior to that of neurofilaments following axotomy. To examine whether proteasome inhibitors would retard Wallerian degeneration in vivo, we applied gelfoams pre-soaked with vehicle (PBS) or MG132 to the lesion sites and examined the transected optic nerves 3 days post-axotomy by immunostaining. Our experimental procedures were adapted from Meyer et al. (1994). In brief, adult mice were anesthetized by an intraperitoneal injection of ketamine (100 mg/kg) and xylazine (20 mg/kg). An incision was then made in the conjunctiva above the left orbit. The optic nerve was exposed under an operating microscope, and its dura opened longitudinally. To study the protective effect of MG132, a gelfoam pre-soaked with PBS or 50 mM MG132 was attached to the lesion site of the optic nerve for 60 min prior to crushing (mimicking the pre-treatment). Using angled jeweler's forceps (Dumont #5; Roboz, Rickville, Md.), the optic nerve was crushed behind the nerve head, avoiding injury to the ophthalmic artery. Gelfoams with MG132 or PBS were kept in the lesion site. Nerve injury was verified by the appearance of a clearing at the crush site; the vascular integrity of the retina was verified by fundoscopic examination after dilating the pupil with atropine. At determined days after nerve crush, the animals were given a lethal dose of anesthesia and perfused through the heart with cold saline plus heparin followed by 4% paraformaldehyde. Eyes with nerve segments up to the optic chiasm still attached were dissected free from connective tissue, postfixed overnight, and transferred to a 30% sucrose solution overnight. Frozen sections (10 mm) were cut longitudinally on a cryostat, thaw-mounted onto coated glass slides (superfrost plus, Fisher, Pittsburgh, USA), and stored at −20° C. until further use.

We found that MG132 significantly slowed the breakdown of microtubules and neurofilaments, as well as axolemma as detected by anti-PGP9.5 antibody staining in transected optic nerves in vivo. These results together indicate that inhibiting UPS activity is able to delay Wallerian degeneration both in vitro and in vivo.

Proteasome inhibitors also delay neurite degeneration in NGF-deprived sympathetic neurons. In addition to transected axons, axons from neurons that have been deprived of their physiological trophic factors may also undergo a Wallerian-like degeneration process (reviewed by Raff et al., 2002). If the distal part of an axon of a cultured sympathetic neuron is locally deprived of NGF, that part of the axon degenerates while the rest of the cell and axon survives (Campenot, 1982). Moreover, it has been shown that such an NGF deprivation-triggered axon degeneration is delayed in the sympathetic neurons from Wld$^s$ mice (Deckwerth and Johnson, 1994). We thus decided to investigate whether UPS is also involved in NGF deprivation-triggered axon degeneration. Consistent with previous studies (for example, Deckwerth and Johnson, 1994), 36 hr after NGF deprivation, all of the cultured sympathetic neurons underwent a typical apoptosis program with death of cell bodies as detected by nuclei staining with Hoechst 33258 (a few normally stained nuclei are glial cells) and degeneration of axons as indicated by both morphological criteria and immunostaining. The caspase inhibitor Z-VAD-fmk efficiently prevented both cell body death and neurite degeneration. However, in the presence of MG132, while these neuronal cell bodies still showed clear apoptotic staining, the majority of the axons were still intact, suggesting that MG132 specifically delays axon degeneration, but not the death of cell bodies. In addition, overexpression of the yeast UBP2 protein by a recombinant HSV also showed a qualitatively similar but less profound protective effect on the degeneration of axons and not the death of cell bodies.

In contrast to microtubule destabilization that is sufficient to induce axon degeneration (for example, Luduena et al., 1986; Wang et al., 2001), previous studies suggested that disruption of neurofilaments by the introduction of anti-NF160 into *Xenopus* embryos did not affect the distribution of microtubule and other axon cytoskeleton structures (Walker et al., 2001). Moreover, we found that, latrunculin B, an actin depolymerizing agent (Spector et al., 1983), failed to induce axon degeneration in our assays. Thus, among the three major polymer components of the axon cytoskeleton, microtubules play a particularly important role in maintaining the integrity of axons. Consistent is the observation of microtubule disruption as the earliest detectable change during the physiological process of axon pruning in *Drosophila* metamorphosis (Watts et al., 2003).

The stability of microtubules in the neurons is controlled by a balance between stabilizing factors, notably microtubule associated proteins (MAPs, including Tau, reviewed by Downing, 2000; Garcia and Cleveland, 2001), and destabilizing factors, including the OP18/stathilin family of protein (Marklund, 1996), the Kin kinesin KIF2 (Desai, 1999) and possibly echinoderm microtubule associated protein (EMAP)-related proteins (Eichenmuller et al., 2002). Upon axotomy, engagement of UPS may lead to microtubule destabilization by degrading the stabilizing factors or the inhibitory molecules of destabilizing factors.

Axonal degeneration has frequently been observed in many types of neurodegenerative diseases and after various neuronal insults (Raff et al., 2002; Coleman and Perry, 2002). Axon degeneration and neuronal cell body apoptosis may operate independently (Deckwerth and Johnson, 1994; Finn et al., 1999). For apoptosis-independent local axon degeneration, a typical example is the "dying back" process in aging Purkinje neurons (Chen and Hillman, 1999) and in peripheral nerves damaged by a wide variety of toxic, metabolic, and infectious insults (Saigoh et al., 1999; Raff et al., 2002). In these cases, axon degeneration begins distally and spreads towards the cell body. Although the underlying mechanisms for these local axon degenerations remain largely unclear, existing evidence supports a potential mechanistic link between such a "dying-back" process and Wallerian degeneration. For instance, the "dying-back" degeneration elicited by vincristine, a clinical anti-tumor drug with a common side effect of inducing axonal degeneration-associated peripheral neuropathy (Schaumburg et al., 1992), is protected in neurons from Wld$^s$ mice (Wang et al., 2001). A mutation in the Uch-11 gene accounts for "dying-back" axon degeneration and the formation of spheroid bodies in degenerating nerve terminals in gad mice (Saigoh et al., 1999); a proposed possibility is that the mutant form of Uch-11 may affect a specific set of substrate proteins (reviewed by MacDonald, 1999). In progressive motor neuronopathy (pmn) mutant mice that develop a progressive caudio-carnial degeneration of their motor neurons from early ages (Schmalbruch et al., 1991), glial cell line-derived neurotrophic factor (GDNF) has been shown to rescue motoneuron cell bodies from apoptosis, but fail to prevent nerve degeneration in pmn/pmn mice (Sagot et al., 1996), and a recent study suggests that inhibiting axon degeneration in these mice by crossing them with Wld$^s$ mice significantly attenuates apoptosis and extends life span (Ferri et al., 2003).

Corticospinal Tract (CST) Regeneration Assay. Proteasome inhibitors are assayed for their ability to improve corticospinal tract (CST) regeneration following thoracic spinal cord injury by promoting CST regeneration into human Schwann cell grafts in the methods of Guest et al. (1997, supra). For these data, the human grafts are placed to span a midthoracic spinal cord transection in the adult nude rat, a xenograft tolerant strain. Inhibitors are incorporated into a fibrin glue and placed in the same region. Anterograde tracing from the motor cortex using the dextran amine tracers, Fluororuby (FR) and biotinylated dextran amine (BDA), are performed. Thirty-five days after grafting, the CST response is evaluated qualitatively by looking for reduced degeneration of CST fibers in or beyond grafts and quantitatively by constructing camera lucida composites to determine the sprouting index (SI), the position of the maximum termination density (MTD) rostral to the GFAP-defined host/graft interface, and the longitudinal spread (LS) of bulbous end terminals. The latter two measures provide information about axonal die-back. In control animals (graft only), the CST do not enter the SC graft and undergo axonal die-back. As shown in Table 2, the exemplified inhibitors dramatically reduce (+++ or ++++) axonal degeneration.

TABLE 2

Neuronal Degeneration with Exemplary Proteasome Inhibitors.

| Proteasome Inhibitor | Reduce Degeneration |
| --- | --- |
| MG-132 (Carbobenzoxy-L-leucyl-L-leucyl-L-leucinal) | +++ |
| MG-115 (Carbobenzoxy-L-leucyl-L-leucyl-L-norvalinal) | ++++ |
| PSI (Carbobenzoxy-L-isoleucyl-γ-t-butyl-L-glutamyl-L-alanyl-L-leucinal) | ++++ |
| Lactacystin (Synthetic: N-Acetyl-L-Cysteine, S-[2R,3S,4R]-3-Hydroxy-2-[(1S)-1-Hydroxy-2-Methylpropyl]-4-Methyl-S-Oxo-2-Pyrolidinecarbonyl]) | +++ |
| PS-519 (clasto-Lactacystin β-Lactone) | ++++ |

TABLE 2-continued

Neuronal Degeneration with Exemplary Proteasome Inhibitors.

| Proteasome Inhibitor | Reduce Degeneration |
|---|---|
| α-Methylomuralide (α-Methyl clasto-Lactacystin β-Lactone) | ++++ |
| MG-101 (Ac-Leu-Leu-Nle-CHO) | +++ |
| MG-262 (Z-Leu-Leu-Leu-B(OH)$_2$) | +++ |
| PS-341 (Velcade; bortezomib) | ++++ |
| Epoxomicin ((2R)-2-[Acetyl-(N-Methyl-L-Isoleucyl)-L-Isoleucyl-L-Threonyl-L-Leucyl]-2-Methyloxirane) | ++++ |

Peripheral nerve regeneration following acute trauma (axotomy). The proteasome inhibitors of Table 2 are also incorporated in the implantable devices described in U.S. Pat. No. 5,656,605 and tested for the promotion of in vivo regeneration of peripheral nerves. Prior to surgery, 18 mm surgical-grade silicon rubber tubes (I.D. 1.5 mm plus Biomatrix 1™, Biomedical Technologies, Inc., Stoughton, Mass) are prepared with or without guiding filaments (four 10-0 monofilament nylon) and loaded with the UPS inhibitors of Table 2.

The sciatic nerves of rats are sharply transected at mid-thigh and guide tubes containing the test substances with and without guiding filaments are sutured over distances of approximately 2 mm to the end of the nerves. In each experiment, the other end of the guide tube is left open. This model simulates a severe nerve injury in which no contact with the distal end of the nerve is present. After four weeks, the distance of regeneration of axons within the guide tube is tested in the surviving animals using a functional pinch test. In this test, the guide tube is pinched with fine forceps to mechanically stimulate sensory axons. Testing is initiated at the distal end of the guide tube and advanced proximally until muscular contractions are noted in the lightly anesthetized animal. The distance from the proximal nerve transection point is the parameter measured. For histological analysis, the guide tube containing the regenerated nerve is preserved with a fixative. Cross sections are prepared at a point approximately 7 mm from the transection site. The diameter of the regenerated nerve and the number of myelinated axons observable at this point are used as parameters for comparison.

Measurements of the distance of nerve regeneration document therapeutic efficacy of the Table 2 inhibitors. Similarly, plots of the diameter of the regenerated nerve measured at a distance of 7 mm into the guide tube as a function of the presence or absence of inhibitors demonstrate a similar therapeutic effect. No detectable nerve growth is measured at the point sampled in the guide tube with the matrix-forming material alone. The presence of guiding filaments (no inhibitor) induces only very minimal regeneration at the 7 mm measurement point, whereas dramatic results, as assessed by the diameter of the regenerating nerve, are produced by the device which consists of the guide tube, guiding filaments and inhibitor. Finally, treatments using guide tubes comprising either a matrix-forming material alone, or a matrix-forming material in the presence of guiding filaments, result in no measured growth of myelinated axons. In contrast, treatments using a device comprising guide tubes, guiding filaments, and matrix containing inhibitor compositions consistently result in axon regeneration, with the measured number of axons being increased markedly by the presence of guiding filaments.

In situ promotion of functional recovery following traumatic cord injury. Table 2 proteasome inhibitors also improve functional recovery and promote regenerative axon growth following traumatic cord injury in a model essentially as described by White, 1998, Neurosci 86, 257–63. The inhibitors promote hyperalgesia when continuously administered intrathecally (into spinal subarachnoid space) for two weeks in normal and traumatized rats. For this, 8 cm of PE 10 tubing is inserted through the cisterna magna in anaesthetized animals (Yaksh et al., 1976, Physiol Behav 17, 1031–36). Rats with and without trauma-induced neurological deficits are used for behavioral and transganglionic labeling studies.

The nociceptive flexion reflex is quantified with an Ugo Basile Analgesymeter (Comerio-Varese, Italy). This device generates a mechanical force that increases linearly with time. The force is applied to the dorsum of the rat's hindpaw, by a cone-shaped plunger (diameter 1.4 mm, radius of curvature 36°). The nociceptive threshold is defined as the force, in grams, at which the rat withdraws its paw. Nociceptive thresholds are determined on a daily basis, five days before and two weeks after the commencement of intrathecal administration of inhibitor or saline, at 10-min intervals for a period of 2 h. The mean of the last six measurements represents the nociceptive threshold for that day. After measuring thresholds on the fifth day, animals are re-anaesthetized and osmotic pumps (0.5 ul/h; 14 days; Alzet, Calif.) are attached to the PE tubing and implanted subcutaneously. All solutions delivered by osmotic pumps contained 10 U/ml heparin and saline served as the vehicle control. These experiments demonstrate that intrathecal administration of the proteasome inhibitors of Table 2 into both normal and traumatized rats induces a significant decrease in threshold to mechanical stimulation in the paw withdrawal test compared to saline-treated control animals.

Intrathecal infusion of lacatacystin B-lactone promotes dorsal column axonal regeneration following upper cervical spinal dorsal hemisection. Intrathecal infusion of the proteasome inhibitors of Table 2 also reduces degeneration of dorsal column ascending axons following spinal cord dorsal hemisection in adult rats. The hemisection is performed between the 3rd and 4th cervical spinal segments ($C_{3-4}$) to a depth of 1.6 mm from the dorsal surface of the cord using a VibraKnife device that can be used to precisely control the lesion depth stereotaxically. To ensure that bilateral dorsal columns are completely transected, the lesion is advanced ventrally to the level of central cannel resulting in the transection of the entire dorsal half of the spinal cord. After the lesion, dura mater is sutured to restore cerebespinal fluid circulation and to prevent connective tissue invasion. Intrathecal delivery of inhibitor (20 uM) or saline vesicle into the lesion site is achieved by constant infusion of the compound at a rate of 0.5 ul/hr for 14 days using an Alzet mini-osmotic pump (Model 2002). Five weeks after surgery, a narrow lesion gap through the dorsal half of the cord is observed, confirming the completeness of dorsal column transection. Unlike conventional lesioning methods that usually cause secondary tissue damage and cavitation, the VibraKnife lesioning results in well-preserved cord stumps with few cavities. Anatomical regeneration of injured dorsal column axons is assessed by anterograde tracing of Cholera toxin B subunit (CTB) which is injected into bilateral sciatic nerves and brachial-plexuses.

In rats that receive inhibitor infusion, CTB-labeled axons are seen to cross the lesion gap and grow within the distal host spinal cord for a considerable distance. Neurolucida reconstruction from a section of inhibitor-treated animals shows the presence of CTB-labeled regenerated axons through and beyond the lesion. After crossing the lesion gap, regenerating dorsal column axons grow back into their original pathway, the dorsal column, and elongate along their tracts for a considerable distance. CTB-labeled axons not only regenerate within the distal dorsal column but also branch into the adjacent gray matter, as do their proximal counterparts. In contrast to the axonal regeneration of the inhibitor-treated group, infusion of vehicle into the lesion gap does not promote axonal regeneration across the lesion gap. In subsequent studies, we similarly show that regenerating axons after proteasome inhibitor treatment are able to establish functional connections with neurons in the dorsal column nuclei, improving physiological and behavioral recovery.

Oral administration of UPS inhibitors prolongs survival and reduces the behavioral and neuropathologicalphenotype in an animal model for Huntington's disease (HD). Efficacy of orally-active proteasome inhibitors lactacystin, α-methylomuralide, PS-519 and PS-341 (Table 2) is also demonstrable in an experimental protocol adapted from Ferrante et al., J. Neurosci. 2000 Jun. 15; 20(12):4389–97. Transgenic male HD mice of the R6/2 strain and littermate controls are bred with females from their background strain (B6 CBAFI/J). Transgene negative and positive R6/2 mice from the same "f" generation are placed on either unsupplemented diets or diets supplemented with 1, 2, or 3% proteasome inhibitor.

Mice are given 2 d to become acquainted with the rotarod apparatus (Columbus Instruments, Columbus, Ohio). Testing commences on day 23. Mice are placed on a rod rotating at 10 rpm. Each mouse is given three trials for a maximum of 180 sec for each trial. The length of time at which the mouse falls off the rotating rod is used as the measure of competency on this task.

After 6–7 hr of fasting, baseline levels of glucose are measured. The mice are lightly anesthetized with isoflurane gas, and tail vein blood collected. The mice are subsequently given a bolus injection of glucose (1.5 gm/kg, i.p.), and plasma glucose levels measured 30 and 60 min later with Lifescan One Touch basic glucose monitoring system (Johnson & Johnson) and validated by semiautomatic glucose oxidase enzyme assay.

Table 3 shows the effects of oral administration of proteasome inhibitors in the diet on survival, rotarod performance, body weight and brain atrophy in HD transgenic mice. The data demonstrate that administration of inhibitor in the diet dose-dependently improves survival. There is also a dose-dependent effect of proteasome inhibitor supplementation on rotarod performance between 21 and 90 d. Similarly, oral administration of proteasome inhibitor significantly improves rotarod performance throughout the entire measured (4–13 weeks) life span of the R6/2 mice in contrast to unsupplemented R6/2 mice. Furthermore, all proteasome inhibitor regimens result in significant improvement of body weight in comparison to unsupplemented R6/2 mice. Finally, gross brain weights of unsupplemented R6/2 mice decreases significantly over time until death in comparison to both transgene-negative littermate control mice and proteasome inhibitor-supplemented R6/2 mice at all time points. Dietary proteasome inhibitor supplementation reduces gross brain atrophy in R6/2 mice in comparison to the untreated R6/2 mice. Consistent with the gross brain weight loss and striatal atrophy, there is significant progressive atrophy of striatal neurons from 21 to 90 d in the unsupplemented R6/2 mice. The cytoprotective effect of proteasome inhibitor significantly delayed striatal neuron atrophy. Furthermore, administration of proteasome inhibitor significantly delays the onset of diabetes as assessed by a glucose tolerance test at 8.5 weeks of age.

TABLE 3

Reduced Degeneration in HD Model.

| Proteasome Inhibitor | Enhanced Survival | Enhanced Body Weight | Enhanced Rotarod Performance | Reduced Brain Atrophy |
| --- | --- | --- | --- | --- |
| Lactacystin | +++ | +++ | +++ | ++++ |
| PS-519 | +++ | ++++ | ++++ | +++ |
| α-Methylomuralide | ++++ | ++++ | ++++ | ++++ |
| PS-341 | ++++ | ++++ | +++ | ++++ |

Proteasome inhibitors reduce brain injury as well as behavioral deficits after middle cerebral artery (MCA) occlusion, modeling ischemic injury. In addition, the inhibitors of Table 2 reduce histological damage due to intrastriatal microinjection of N-methyl-D-aspartate (NMDA) or α-amino-3-hydroxy-5-methyl-4-isoxazole propionate (AMPA), a model of excitotoxic brain damage in stroke and neurodegenerative disorders. Our experimental protocol was adapted from Hara, et al. Proc. Natl. Acad. Sci. USA. 1997 Mar. 4; 94 (5): 2007–2012.

Regional cerebral blood flow (rCBF) is determined by laser-Doppler flowmetry using a flexible 0.5-mm fiber optic extension to the master probe affixed over the ischemic cortex on the intact skull. rCBF, blood pressure, and heart rate are monitored, and heart rate is monitored from the arterial blood pressure pulse. Arterial blood samples are analyzed for oxygen (PaO2) and carbon dioxide (PaCO2) before and during ischemia and 30 min after reperfusion using a blood gas/pH analyzer. Core temperature is maintained at approximately 37C. with a thermostat and a heating lamp until 1 hr after reperfusion. In the rat experiments, rCBF, blood pressure, and heart rate are determined as described above.

Ischemia Model: Mouse. Spontaneously ventilating adult male SV-129 mice are initially anesthetized with 1.0% and maintained on 0.4 0.8% halothane in 70% N2O and 30% O2 using a Fluotec 3 vaporizer (Colonial Medical, Amherst, N.H.). The left MCA is occluded with an 8-0 nylon monofilament coated with a mixture of silicone resin and a hardener. Two hours later, animals are briefly re-anesthetized with halothane, and the filament withdrawn. Eighteen hours after reperfusion, the forebrains are divided into five coronal (2-mm) sections using a mouse brain matrix, and the sections stained with 2% 2,3,5-triphenyltetrazolium chloride. The infarcted areas are quantitated by an image-analysis system and calculated by summing the volumes of each section determined directly or indirectly by the following formula: contralateral hemisphere ($mm^3$)—ipsilateral undamaged volume ($mm^3$). Brain swelling is calculated according to the following formula: [(infarct volume+ipsilateral undamaged volume−contralateral volume)×100/contralateral volume (%)]. For histological evaluation of neuronal damage at 18 hr and 3 days after ischemia, sections (12 um) are stained with hematoxylin/eosin.

Inhibitors (13.5, 40, or 120 ng) are injected intracerebroventricularly (i.c.v.) twice (2 ul per dose; bregma: 0.9 mm lateral, 0.1 mm posterior, 3.1 mm deep) 15 min before ischemia and immediately after reperfusion.

Ischemia Model: Rat. Adult male Sprague Dawley rats are initially anesthetized with 2.0% and maintained by 1.0% halothane in 70% N2O and 30% $O_2$ using a Fluotec 3 vaporizer. The left MCA is occluded with a 3-0 nylon monofilament with its tip rounded by heating near a flame. The filament is inserted from the left external carotid artery and advanced into the internal carotid artery. The distance from the suture tip to the left common carotid artery bifurcation is approximately 20 mm. Two hours after ischemia, animals are briefly re-anesthetized with halothane, and the filament withdrawn. Twenty-two hours later, the brains are stained with 2,3,5-triphenyltetrazolium chloride for morphometric analysis. Inhibitors (8, 27, or 80 ng) are injected i.c.v. 15 min before ischemia and 10 min after reperfusion in 2 equal doses.

Mice and rats are tested for neurological deficits and scored as follows: 0, no observable neurological deficits (normal); 1, failure to extend right forepaw (mild); 2, circling to the contralateral side (moderate); 3, loss of walking or righting reflex (severe).

UPS inhibitors injected into the ventricle 15 min before and upon reperfusion, result in a significant reduction in infarct size: infarct size ranges from 76 to 128 $mm^3$ in vehicle-treated brains, whereas values ranged from 31 to 80 $mm^3$ after treatment with 240 ng of inhibitors. Infarct sparing is particularly noted in posterior forebrain (coronal sections from 6 to 10 mm). Neurological deficits are significantly reduced after 18 hr but not immediately upon reperfusion. Neuroprotection is sustained for at least 3 days.

Protection is also observed when the inhibitors (40 ng×2) are administered before and upon reperfusion. For these data, we inject inhibitors upon reperfusion after 2 hr of occlusion. Inhibitors (80 ng), administered as a single dose, diminished infarct size. Sparing is observed in the three coronal sections. Similar results are obtained in rats. For these data, the inhibitor is injected into the lateral ventricle of Sprague Dawley rats 15 min before ischemia (2 hr of MCA occlusion) and upon reperfusion. Again, the proteasome inhibitors (54 and 160 ng) of Table 2 significantly reduce infarct volume in rat cortex and striatum and decreased neurological deficits.

Proteasome inhibitors reduce neurodegeneration in an ALS transgenic mouse model. Reduced axon degeneration by proteasome inhibition is also evident in transgenic mice expressing mutant human copper/zinc superoxide dismutase (SOD1) with a substitution of glycine to alanine in position 93 (mSOD1$^{G93A}$)—an animal model of familial amyotrophic lateral sclerosis (ALS)— in an experimental protocol modeled after that of Li, et al. (2000, Science 288, 335–339), wherein intracerebroventricular administration of the proteasome inhibitors of Table 2 delays disease onset and mortality.

Osmotic pumps (Alzet, Palo Alto, Calif.) deliver the inhibitors into the cerebral ventricle of 60-day-old mice. At this age there is no significant neuronal loss, clinically representing the late presymptomatic stage of the disease. Pumps are filled with vehicle (0.4% dimethyl sulfoxide, 0.1 M Pipes, pH 6.9), 10 $\mu$g of inhibitor per 20 g body weight, or 30 $\mu$g of inhibitor per 20 g of body weight. Pumps continuously deliver the inhibitor for 28 days and are then exchanged for new pumps filled with fresh inhibitor or vehicle for an additional 28-day treatment. The onset of motor and/or coordination deficits is defined as the first day that a mouse can not remain on the Rotarod (Columbus Instruments, Columbus, Ohio): mice are first evaluated the day before placement of the osmotic pumps and thereafter on a weekly basis. Mice are placed on the rotating rod at speeds of 5, 15, and 20 rpm. The time each mouse remains on the rod is registered automatically. If the mouse remains on the rod for 7 min, the test is completed and scored as 7 min.

Mortality is scored as the age of death or the age when the mouse is unable to right itself within 30 s. The length of time before disease onset in transgenic mice treated with either vehicle or 30 $\mu$g of inhibitor per 20 g of body weight for 28 days is approximately 10 days and 120 days, respectively; hence, inhibitor delays the disease-induced onset of Rotarod deficit by about 20 days. In addition, inhibitor treatment prolongs survival from 120 days to 150 days as compared with vehicle-treated littermates, representing a life-span prolonged by 20%. Inhibitor-mediated neuroprotection is dose-dependent and motor strength and coordination, as evaluated by Rotarod performance, are significantly improved in inhibitor-treated mice.

To evaluate the effect of the inhibitors on motor neuron loss, we compare the numbers of cervical and lumbar motor neurons in both inhibitor- and vehicle-treated mSOD1$^{G93A}$ mice. Spinal cord and phrenic nerve samples are collected and processed as described by Kostic, et al., (1997, Science 277, 559). Motor neurons are counted on cryostat-cut sections (40 um thick) stained with thionin. Quantification is performed by stereology as described by Liberatore et al. (Nature Med. 5, 1403 1999) on every 10th spinal cord section, spanning the entire cervical and lumbar enlargements. At 110 days of age, vehicle-treated mice are at the end stage of the disease. Inhibitor-treated mice have a significantly greater number of motor neurons at the cervical level as compared with vehicle-treated mice. At the lumbar level, inhibitor-treated mice also have a greater number of motor neurons. Degeneration of phrenic nerve axons is also significantly inhibited in inhibitor-treated mice.

References

Andreu J M, Timasheff S N. (1986). Ann N Y Acad Sci 466, 676–689.
Baker R T, Tobias J W, Varshavsky A. (1992). J Biol Chem 1992 Nov. 15;267(32):23364–75
Bence, N. F., Sampat, R. M., and Kopito, R. R. (2001). Science 292, 1552–1555.
Campbell D S, Holt C E. (2001). Neuron 32, 1013–1026.
Campbell D S, Holt C E. (2003). Neuron 37, 939–952.
Chen, S. and Hillman, D. E. (1999). J Neurocytol 28, 187–196.
Coleman, M., and Perry, V. H. (2002). Trends Neurosci 25,532-
Conforti, et al. (2000). Proc Natl Acad Sci USA 97, 11377–11382.
DiAntonio A, et al. (2001). Nature 412, 449–452.
Deckwerth T L, Johnson E M Jr. (1994). Dev Biol 165, 63–72.
Desai A, Verma S, Mitchison T J, Walczak C E. (1999). Cell 96, 69–78.
Downing K H. (2000). Annu Rev Cell Dev Biol 16, 89–111.
Eichenmuller et al. (2002). J Biol Chem 277, 1301–1309.
Fenteany G, et al. (1995). Science 268, 726–731.
Ferri A, et al. (2003). Curr Biol 13, 669–673.
Finn, J. T., et al. (2000). J Neurosci 20, 1333–1341.
Friedlander, R. M. (2003). New Eng J Med 348, 1365–1375.
Garcia M L, Cleveland D W. (2001). Curr Opin Cell Biol 13, 41–48.
George, E. B., Glass, J. D., and Griffin, J. W. (1995). J Neurosci 15, 6445–6452.
Gillingwater T H, Ribchester R R. (2001). J Physiol 534(Pt 3):627–639.

Glass, J. D., et al. (1993). J Neurocytol 22, 311–321.
Glass, J. D., Culver, D. G., Levey, A. I., and Nash, N. R. (2002). J. Neurologic Sci 196, 9–20.
Glickman M H, Ciechanover A. (2002). Physiol Rev 82, 373–428.
Griffin, et al., In: Waxman S W, Kocsis, J. D., Stys, P. K., editors. The axon. New York: Oxford Univ. Press; 1995. p375–390.
He Z, Zhai Q and Wang J. (2003) Unpublished data.
Jacob J M, McQuarrie I G. (1996). J Neurosci Res 43, 412–419.
Kamakura K, Ishiura S, Sugita H, Toyokura Y. (1983). J Neurochem 40, 908–913.
Koegl, et al. (1999). Cell 96, 635–644.
Luduena, et al. (1986). Ann N Y Acad Sci 466, 718–732.
Lund L M, Machado V M, McQuarrie I G. (2002) Exp Neurol 178, 306–312.
Lunn, et al., (1988). Euro J Neurosci 1, 27–33.
MacDonald M E. (1999). Nat Genet 23, 10–11.
Mack, T. G., Reiner, M., Beirowski, B., Mi, W., Emanuelli, M., Wagner, D., Thomson, D., Gillingwater, T., Court, F., Conforti, L., et al. (2001). Nat Neurosci 4, 1199–1206.
Marklund et al. (1996). EMBO J. 15, 5290–5298.
Meyer, R. L., Miotke, J. A., Benowitz, L. I. (1994). Neuroscience 63, 591–602.
Miller R J and Wilson S M (2003) Trends Pharmacol Sci 24, 18–23.
Perry, et al. (1990a).Eur J Neurosci 2, 408–413.
Perry V H, Brown M C, Lunn ER, Tree P, Gordon S. (1990b) Eur J Neurosci 2, 802–808.
Pronk G J, Ramer K, Amiri P, Williams L T. (1996). Science 271, 808–810.
Raff, M. C., Whitemore, A. V., and Fini, J. T. (2002). Science 296,868–871.
Rock et al. Cell 78, 761–771.
Ruckdeschel et al.(1998). J Exp Med 187, 1069–1079.
Sagot Y, Tan SA, Hammang J P, Aebischer P, Kato A C. (1996). J Neurosci 16, 2335–2341.
Saigoh, K., Wang, Y. L., Suh, J. G., Yamanishi, T., Sakai, Y., Kiyosawa, H., Harada, T., Ichihara, N., Wakana, S., Kikuchi, T., and Wada, K. (1999). Nat Genet 23, 47–51.
Sanchez et al. (1992). J Biol Chem 267, 24725–24731.
Schaumburg, H H, Berger, A R, and Thomas, P K. (1992). F. A. Davis, Philadelphia.
Schlaepfer W W, Hasler M B. (1979). Brain Res 168, 299–309.
Schlaepfer W W, Micko S. (1978). J Cell Biol 78, 369–378.
Schlaepfer W W, Lee C, Trojanowski J Q, Lee V M. (1984). J Neurochem 43, 857–864.
Schmalbruch et al. (1991). J Neuropathol Exp Neurol 50, 192–204.
Sotelo C. (1990). J Neurocytol 19, 737–755.
Spector I, Shochet N R, Kashman Y, Groweiss A. (1983). Science 219, 493–495.
Suetsugu et al. (2002). Dev Cell 3. 645–658.
Walker, K. L., Yoo, H. K., Undamatla, J., Szaro, B. G. (2001). J. Neurosci 15, 9655–9666.
Waller, A. (1850). Phil Trans R Soc Lond 140, 423–429.
Wang M, Wu Y, Culver DG, Glass JD. (2001). Neurobiol Dis 8, 155–161.
Wang, et al. (2001). Ann Neurol 50, 773–779.
Watts, R J, Hoopfer, E. D., Luo, L. (2003). Neuron (accepted for publ June 18 issue).
Weissman, A. M. (2001). Nat Rev Mol Cell Biol 2, 169–178.
Wilson L, Farrell K W. (1986). Ann N Y Acad Sci 466, 690–708.
Yuan J, Yankner B A. (2000). Nature 407, 802–809.

The foregoing descriptions of particular embodiments and examples are offered by way of illustration and not by way of limitation. All publications and patent applications cited in this specification and all references cited therein are herein incorporated by reference as if each individual publication or patent application or reference were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method of reducing degeneration of an axon predetermined to be subject to degenerative neuropathy in a term patient, the method comprising:
contacting the axon in situ with an effective amount of a ubiquitin-proteasome system (UPS) inhibitor sufficient to reduce degeneration of the axon; and
detecting a resultant reduction in the degeneration of the axon in situ,
wherein the inhibitor is a proteasome inhibitor selected from the group consisting of:
MG-132 (Carbobenzoxy-L-leucyl-L-leucyl-L-leucinal),
MG-115 (Carbobenzoxy-L-leucyl-L-leucyl-L-norvalinal),
PSI(Carbobenzoxy-L-isoleucyl-γ-t-butyl-L-glutamyl-L-alanyl-L-leucinal),
Lactacystin (Synthetic: N-Acetyl-L-Cysteine, S-[2R,3 S,4R]-3-Hydroxy-2-[(1S)-1-Hydroxy-2-Methylpropyl]-4-Methyl-5-Oxo-2-Pyrolidinecarbonyl]),
PS-519 (clasto-Lactacystin β-Lactone),
α-Methylomuralide(α-Methyl clasto-Lactacystin β-Lactone),
MG-101 (Ac-Leu-Leu-Nle-CHO),
MG-262 (Z-Leu-Leu-Leu-B(OH)2),
PS-341 (Velcade; bortezomib), and
Epoxomicin ((2R)-2-[Acetyl-(N-Methyl-L-Isoleucyl)-L-Isoleucyl-L-Threonyl-L-Leucyl]-2-Methyloxirane),
wherein the degenerative neuropathy is axon trauma or axotomy, and
wherein the contacting is effected by local, regionally-restricted delivery of the inhibitor proximate to the axon.

2. The method of claim 1, wherein the delivery is effected with a slow release gel-foam or osmotic pump.

3. The method of claim 1, wherein the contacting step avoids contact with the cell body of a neuron comprising the axon.

4. The method of claim 1, wherein the degenerative neuropathy is in the absence of substantial neuro-necrosis.

5. The method of claim 1, wherein the method consists essentially of the recited contacting and detecting steps.

6. The method of claim 1, wherein the inhibitor is delivered in conjunction with a microtubule stabilizing reagent.

7. The method of claim 1, wherein preceding the contacting step, the method comprises diagnosing the neuropathy.

8. The method of claim 1, wherein the axon is a central nervous system (CNS) axon.

9. The method of claim 1, wherein the axon is a peripheral nervous system (PNS) axon.

10. The method of claim 1, wherein the inhibitor is MG-132.

11. The method of claim 1, wherein the inhibitor is MG-115.

12. The method of claim 1, wherein the inhibitor is PSI.

13. The method of claim 1, wherein the inhibitor is Lactacystin.

14. The method of claim 1, wherein the inhibitor is PS-519.

15. The method of claim 1, wherein the inhibitor is α-Methylomuralide.

16. The method of claim 1, wherein the inhibitor is MG-101.

17. The method of claim 1, wherein the inhibitor is MG-262.

18. The method of claim 1, wherein the inhibitor is PS-341.

19. The method of claim 1, wherein the inhibitor is Epoxomicin.

* * * * *